US012031980B2

(12) United States Patent
Castrop

(10) Patent No.: US 12,031,980 B2
(45) Date of Patent: Jul. 9, 2024

(54) SYNTHETIC ANTIGENS FOR TUBERCULOSIS DETECTION

(71) Applicants: KEI INTERNATIONAL LIMITED, Hong Kong (HK); TOMORROWS IP LIMITED, Hong Kong (HK)

(72) Inventor: Johannes Theodorus Castrop, Woudenberg (NL)

(73) Assignees: KEI INTERNATIONAL LIMITED, Hong Kong (HK); TOMORROWS IP LIMITED, Hong Kong (HK)

( * ) Notice: Subject to any disclaimer, the term of this patent is extended or adjusted under 35 U.S.C. 154(b) by 724 days.

(21) Appl. No.: 17/266,970

(22) PCT Filed: Aug. 8, 2019

(86) PCT No.: PCT/CN2019/099736
§ 371 (c)(1),
(2) Date: Feb. 8, 2021

(87) PCT Pub. No.: WO2020/030034
PCT Pub. Date: Feb. 13, 2020

(65) Prior Publication Data
US 2021/0293804 A1 Sep. 23, 2021

(30) Foreign Application Priority Data
Aug. 8, 2018 (NL) .................................. 2021443

(51) Int. Cl.
G01N 33/543 (2006.01)
C07H 19/16 (2006.01)
G01N 33/569 (2006.01)

(52) U.S. Cl.
CPC ....... G01N 33/54373 (2013.01); C07H 19/16 (2013.01); G01N 33/5695 (2013.01)

(58) Field of Classification Search
CPC ......... G01N 33/54373; G01N 33/5695; C07H 19/16
See application file for complete search history.

(56) References Cited

U.S. PATENT DOCUMENTS

| 5,597,735 | A | 1/1997 | Laszlo et al. ................. 436/525 |
| 5,721,109 | A | 2/1998 | Yano et al. ................... 435/7.32 |
| 6,416,962 | B1 | 7/2002 | Das et al. .................... 435/7.32 |
| 7,851,166 | B2 | 12/2010 | Verschoor et al. ............ 435/7.2 |
| 8,030,088 | B2 | 10/2011 | McCash et al. ............... 436/164 |
| 10,921,322 | B2 | 2/2021 | Castrop ............ G01N 33/56933 |
| 2003/0143652 | A1 | 7/2003 | Simonson ..................... 435/7.32 |
| 2004/0132106 | A1 | 7/2004 | Houthoff et al. .............. 435/7.1 |
| 2007/0243557 | A1 | 10/2007 | Friedman et al. ............. 435/7.1 |
| 2008/0064051 | A1 | 3/2008 | Hasnain et al. .............. 435/7.92 |
| 2009/0111125 | A1 | 4/2009 | Verschoor .................... 435/7.21 |
| 2011/0280930 | A1 | 11/2011 | Batista et al. ................ 424/450 |
| 2012/0301510 | A1 | 11/2012 | Kishimoto et al. .......... 424/400 |
| 2019/0219574 | A1* | 7/2019 | Castrop .................. C07H 11/04 |

FOREIGN PATENT DOCUMENTS

| CN | 102707053 | 10/2012 | ........... G01N 33/543 |
| CN | 102818889 | 12/2012 | ........... G01N 33/545 |
| EP | 0921397 | 6/1999 | ........... G01N 33/569 |
| EP | 1950218 | 7/2008 | ............. C07H 13/06 |
| EP | 2272860 | 1/2011 | ........... G01N 33/543 |
| EP | 2416158 | 2/2012 | ........... G01N 33/543 |
| NL | 2017204 | 7/2016 | ........... G01N 33/569 |
| RU | 2470801 | 6/2011 | ............... B60P 3/00 |
| WO | WO9414069 | 6/1994 | ........... G01N 33/569 |
| WO | WO9424560 | 10/1994 | ........... G01N 33/543 |
| WO | WO2004112694 | 12/2004 | |
| WO | WO2005116654 | 12/2005 | ........... G01N 33/569 |
| WO | WO2006026404 | 3/2006 | |
| WO | WO2009133378 | 11/2009 | ........... G01N 33/543 |
| WO | WO2010008667 | 1/2010 | ............. A61L 27/54 |
| WO | WO2012119128 | 3/2012 | ................ B01L 3/00 |
| WO | WO2012151039 | 11/2012 | ......... A61K 31/6615 |
| WO | WO2013186679 | 12/2013 | ........... G01N 33/543 |
| WO | WO2014184768 | 11/2014 | ........... G01N 33/569 |
| WO | WO2014210327 | 12/2014 | ............. A61K 31/06 |
| WO | WO2016024116 | 2/2016 | ........... G01N 33/543 |
| WO | WO2017/211316 | * 12/2017 | |
| WO | WO2017211314 | 12/2017 | ........... G01N 33/543 |
| WO | WO2017211316 | 12/2017 | ........... G01N 33/569 |

OTHER PUBLICATIONS

Angala et al., The cell envelope glycoconjugates of *Mycobacterium tuberculosis*, Critical Reviews in Biochemistry and Molecular Biology, 2017 (40 pgs).
Astarie-Dequeker et al., The role of mycobacterial lipids in host pathogenesis, Drug Discover Today: Disease Mechanisms,, vol. 7, No. 1, 2010 (9 pgs).
Boulous et al. Journal of Publich Health Infomatics 5(3) 2014.
Buter et al., Stereoselective Synthesis of 1-Tuberculosinyl Adenosine; a Virulence Factor of *Mycobacterium tuberculosis*, J Org Chem, 2016, 81(15) (25 pgs).
Camacho et al., "Phage display of functional αβ single-chain T-cell receptor molecules specific for CD1b:Ac₂SGL complexes from *Mycobacterium tuberculosis*-infected cells", BioMed Central, BMC Immunology 2013, 14 (Suppl 1): 52 (4 pages).
Chamanzar et al., "Hybrid photonic surface-plasmon-polariton ring resonators for sensing applications," Applied Physics B, vol. 101, No. 1-2, Oct. 2010, pp. 263-271 (9 pgs).
Cruaud et al., "Human IgG Antibodies Immunoreacting with Specific Sulfolipids from *Mycobacterium tuberculosis*", Zbl. Bakt. 271, 481-485 (1989) (5 pgs).
Dang et al., "Direct detection of *Mycobacterium tuberculosis* in sputum using combined solid phase extraction-gas chromatography-mass spectrometry", Journal of Chromatography B, pp. 986-987 (2015) 115-122 (8 pages).

(Continued)

Primary Examiner — Timothy R Rozof
(74) Attorney, Agent, or Firm — HAYES SOLOWAY P.C.

(57) ABSTRACT

Disclosed is a synthetic antigen and a solid substrate having an antigen immobilized thereto and a method for immobilizing the antigen onto a solid substrate. Also disclosed is a biosensor and tuberculosis detection system employing the said solid substrate. Also disclosed is a method of detecting the presence of antibodies against mycobacterial material in a sample using the synthetic antigen or solid substrate.

27 Claims, 1 Drawing Sheet

(56) References Cited

OTHER PUBLICATIONS

De Jong et al., "CD1c Presentation of Synthetic Glycolipid Antigens with Foreign Alkyl Branching Motifs," Chemistry & Biology 14, 1232-1242, Nov. 2007 (11 pgs).
De Libero et al., "Recognition of Lipid Antigens by T Cells," Nature Reviews/Immunology, vol. 5, Jun. 2005 (12 pgs).
Egorov, "Physicochemical Patterns of Antigen-Antibody Interactions", Chapter 2, pp. 33-35 with English Translation (4 pages).
European Search Report for Application Serial No. 17 80 9753, dated Oct. 4, 2019 (5 pages).
Garźon et al., Predicted structural basis for CD1c presentation of mycobacterial branched polyketides and long lipopeptide antigens, Molecular Immunology 47 (2009) 253-260 (8 pgs).
Geerdink et al., Total synthesis, stereochemical elucidation and biological evaluation of $Ac_2SGL$; a 1,3-methyl branched sulfoglycolipid from *Mycobacterium tuberculosis*, Chemical Science, No. 2, 2013, abstract only (3 pgs).
Gilleron et al., Diacylated Sulfoglycolipids Are Novel Mycobacterial Antigens Stimulating CD1-restricted T Cells during Infection with *Mycobacterium tuberculosis*, The Journal of Experimental Medicine, 2004 (11 pgs).
Hamilton et al., "Naturally occurring carbohydrate antibodies: Interference in solid-phase imunoassays" *Journal of Immunological Methods*, vol. 77, Issue 1, Feb. 28, 1985, pp. 95-108, Abstract only (2 pgs).
Hermanson, G., "Bioconjugate Techniques," Academic Press, 3$^{rd}$ Edition, Aug. 2013, book description only (3 pgs).
Huebner, Johannes, "Antibody-Antigen Interaction and Measurements of Immunologic Reactions", Chapter 9, 2004(26 pages).
International Preliminary Report on Patentability issued in application No. PCT/NL2016/050002, dated Dec. 19, 2016 (30 pgs).
International Preliminary Report on Patentability issued in application No. PCT/CN2017/087547, dated Dec. 11, 2018 (8 pgs).
International Preliminary Report on Patentability issued in application No. PCT/CN2019/099736, dated Feb. 9, 2021 (7 pgs).
International Preliminary Report on Patentability issued in application No. PCT/CN2019/124224, dated Mar. 19, 2021 (4 pgs).
International Search Report and Written Opinion issued in application No. PCT/CN2017/087547, dated Aug. 28, 2017 (13 pgs).
International Search Report and Written Opinion issued in application No. PCT/CN2019/124224, dated Mar. 6, 2020 (11 pgs).
International Search Report and Written Opinion issued in application No. PCT/NL2016/050002, dated Jun. 30, 2016 (13 pgs).
International Search Report and Written Opinion issued in application No. PCT/CN2017/087542, dated Aug. 18, 2017 (11 pgs).
International Search Report and Written Opinion issued in application No. PCT/CN2019/099736, dated Nov. 6, 2019 (11 pgs).
International Search Report and Written Opinion issued in application No. NL2022166, dated Dec. 10, 2018 (11 pgs).
International Search Report and Written Opinion issued in application No. NL2021443, dated Mar. 27, 2019 (11 pgs).
Jain et al. 2017 "The principals and applications of avidin-based nanoparticles in drug delivery and diagnosis", J. Control Release Jan. 10, 2017; 245: 27-40 (36 pgs).
Julian et al. 2004 (Comparison of Antibody Responses to a Potential Combination of Specific Glycolipids and Proteins for Test Sensitivity Improvement in Tuberculosis Serodiagnosis; Clinical and Diagnostic Laboratory Immunology 11 (1): 70-76). (Year: 2004).
Julian et al. 2001 (An ELISA for five glycolipids from the cell wall of Mycobacteriumn W tuberculosis: Tween 20 interference in the assay; Journal of Immunological Methods 251: 21-30) (Year: 2001).
Julian et al. 2002 (Serodiagnosis of Tuberculosis: Comparison of Immunoglobulin A (IgA) Response to Sulfolipid I with IgG and IgM Responses to 2,3-Diacyltrehalose, 2,3,6-Triacyltrehalose, and Cord Factor Antigens, Journal of Clinical Microbiology, Oct. 2002, pp. 3782-3788 (7 pages).

Kim et al., "Diagnosis of Tuberculosis Using a Liquid Crystal-Based Optical Sensor", Macromolecular Research, The Polymer Society of Korea and Springer, Nov. 2015 (8 pages).
Laszio et al. 1992 (Comparison of Bis-di-octadecylamide of trehalose Dicarboxylic Acid (BDA.TDA) with glycolipid SL-IV as ELISA antigens for the serodiagnosis of Leprosy; International Journal of Leprosy; 60(3):376-381). (Year: 1992).
Law, B., "Immunoassay: a practical guide," Taylor & Francis e-Library, 2005 (15 pgs).
Layre et al., Molecular profiling of *Mycobacterium tuberculosis* identifies tuberculosinyl nucleoside products of the virulence-associated enzyme Rv3378c, PNAS, 2014, vol. 11, No. 8, 2978-2983 (6 pgs).
Lemmer et al., "Detection of Antimycolic Acid Antibodies by Liposomal Biosensors," Methods in Enzymology, No. 464, Jan. 2009, pp. 79-104 (26 pgs).
Li et al., Highly Stereocontrolled Total Synthesis of β-$_D$-Mannosyl Phosphomycoketide: A Natural Product from *Mycobacterium tuberculosis*, The Journal of Organic Chemistry, 2013, 78, 5970-5986 (17 pgs).
Mathebula et al., "Recognition of anti-mycolic acid antibody at self-assembled mycolic acid antigens on a gold electrode: a potential impedimetric immunosensing platform for active tuberculosis," Chemical Communications, No. 23, May 2009, pp. 3345-3347 (3 pgs).
Matsunaga et al., Mycoketide: A CD1c-Presented Antigen with Important Implications in Mycobacterial Infection, Clinical and Developmental Immunology, 2012 (8 pgs).
Moody et al., "CD1c-mediated T-cell recognition of isoprenoid glycolipids in *Mycobacterium tuberculosis* infection," Nature, vol. 404, Apr. 20, 2000 (5 pgs).
Office Action issued in U.S. Appl. No. 16/307,427, dated Mar. 10, 2021, 56 pages.
Office Action issued in U.S. Appl. No. 16/307,422, dated Jun. 1, 2021, 22 pages.
Office Action issued in U.S. Appl. No. 16/307,422, dated Aug. 13, 2020, 32 pages.
Office Action issued in U.S. Appl. No. 16/307,422, dated Mar. 6, 2020, 23 pages.
Pavlickova P., Hug H. (2004) A Streptavidin-Biotin-Based Microarray Platform for Immunoassays. In: Fung E.T. (eds) Protein Arrays. Methods in Molecular Biology, vol. 264. Humana Press. https://doi.org/10.1385/1-59259-759-9:073 (Abstract and Fig 2 only).
Thanyani et al., "A novel application of affinity biosensor technology to detect antibodies to mycolic acid in tuberculosis patients," Journal of Immunological Methods, vol. 332, Jan. 2008, pp. 61-72 (12 pgs).
Thanyani, S.T., "An assessment of two evanescent field biosensors in the development of an immunoassay for tuberculosis," partial fulfillment of the requirements for the PhD Degree in Biochemistry in the Faculty of Natural & Agricultural Sciences, University of Pretoria, Jul. 2008 (194 pgs).
Tiwari et al., "Glycolipids of *Mycobactrium tuberculosis* Strain H37Rv Are Potential Serological Markers for Diagnosis of Active *tuberculosis*," Clinical and Diagnostic Laboratory Immunology, vol. 12, No. 3, Mar. 2005, pp. 465-473 (9 pgs).
Van Summeren et al., Total Synthesis of Enantiopure β-D-Mannosyl Phosphomycoketides from *Mycobacterium tuberculosis*, J. Am. Chem. Soc., 2006, 128, 4546-4547 (2 pgs).
Young et al., In Vivo Biosynthesis of Terpene Nucleosides Provides Unique Chemical Markers of *Mycobacterium tuberculosis* Infection, Chemistry & Biology 22, 2015, 516-526 (12 pgs).
U.S. Appl. No. 17/312,887, filed Jun. 10, 2021, Castrop.
U.S. Appl. No. 16/307,422, filed Dec. 5, 2018, Castrop.
U.S. Appl. No. 16/307,427, filed Dec. 5, 2018, Castrop.
Castan et al., Point-of-care system for detection of *Mycobacterium tuberculosis* and rifampin resistance in sputum samples:, J. Chin. Microbiol., 2014, vol. 52, No. 2, pp. 502-507.
Office Action issued in U.S. Appl. No. 16/307,427, dated Nov. 17, 2021, 34 pages.

* cited by examiner

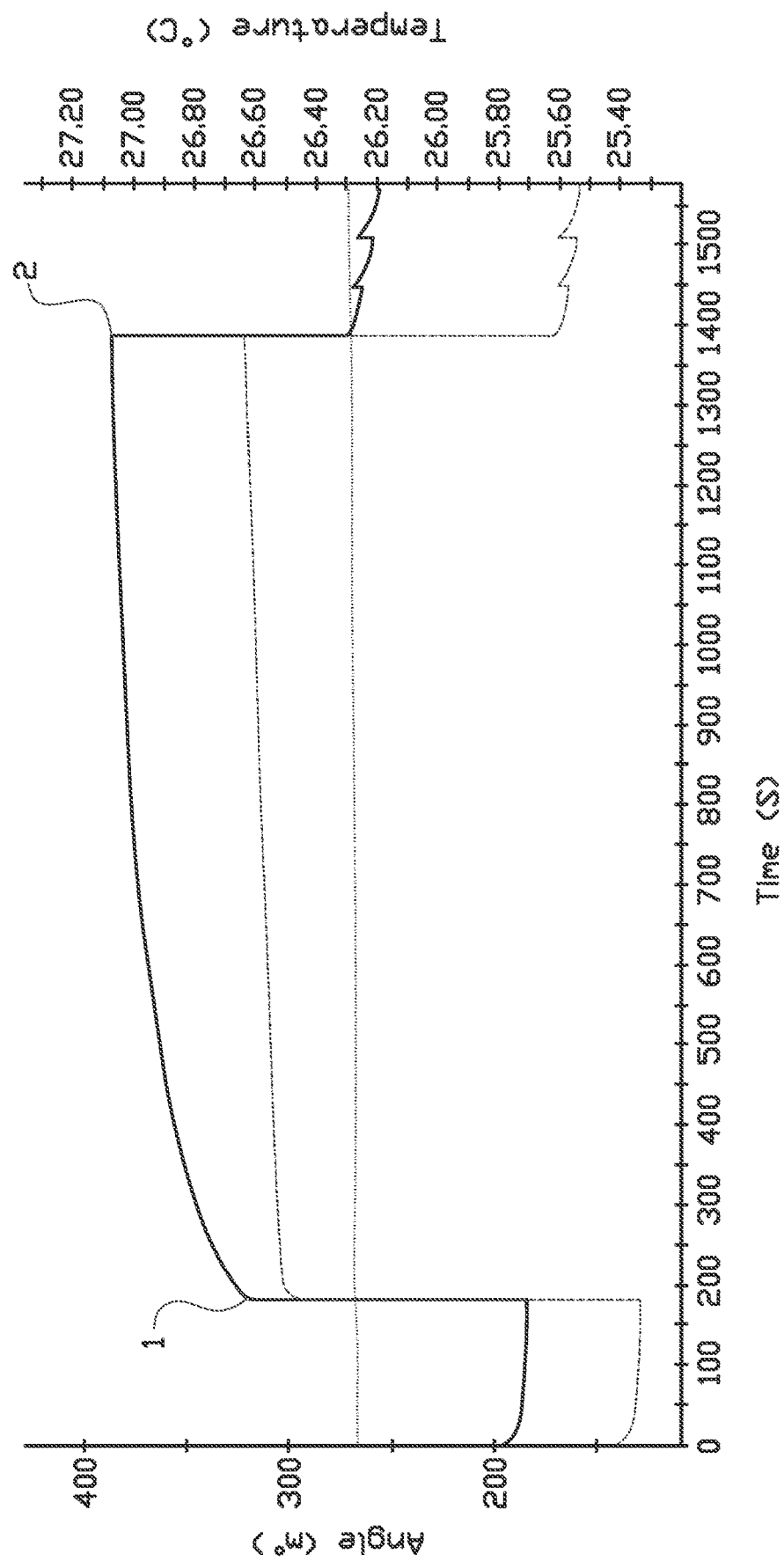

SYNTHETIC ANTIGENS FOR TUBERCULOSIS DETECTION

The present invention relates to a synthetic antigen and a solid substrate comprising an antigen immobilized thereto and a method for immobilizing said antigen onto a solid substrate. The invention also relates to a biosensor and tuberculosis detection system comprising said solid substrate. The invention also relates to a method of detecting the presence of antibodies against mycobacterial material in a sample using said synthetic antigen or solid substrate.

INTRODUCTION

*Mycobacterium tuberculosis* is a pathogenic bacterial species in the family Mycobacteriaceae and the causative agent of most cases of tuberculosis (TB).

TB is still one of the leading causes of death in many low and middle income countries. In addition, more and more cases are reported of multi-drug resistant TB.

A reliable and fast way of diagnosing tuberculosis is therefore of utmost importance.

Several methods of diagnosing tuberculosis have been developed, but all methods have their disadvantages.

Humans or animals infected with *M. tuberculosis* normally produce antibodies directed against the *Mycobacterium*. The presence of these antibodies in a sample taken from infected individuals indicates the infection. The most common *Mycobacterium* specific antigens are mycolic acids or derivatives thereof. For instance, WO 2005/116654 and WO 2013/186679 describe methods of antibodies in a sample against mycolic acids for the diagnosis of active tuberculosis, by detecting binding of antibodies to immobilized mycolic acid antigens.

Another type of antigen of particular interest in this respect comprises tuberculosinyl adenosine (TbAd) antigens and derivatives thereof.

Dutch patent NL 2017204 C1 in the name of the same applicants as the present invention describes immobilized tuberculosinyl adenosine antigens in combination with other types of antigens for use in detection of the presence of antibodies against mycobacterial material in a sample. The presence of mycobacterial material in the sample indicates tuberculosis in the subject from which the sample was derived.

The inventor however considers that there is room for improvement with respect to the sensitivity of detection of tuberculosis.

SUMMARY OF THE INVENTION

The inventor has now found that antigen presentation of tuberculosinyl adenosine antigens can be significantly improved by the provision of a linker group at the position where native tuberculosinyl adenosine antigens (1-tuberculosinyladenosine) have a hydroxymethyl group on the adenosine moiety and immobilizing the antigens to a solid substrate via said linker.

Therefore in a first aspect the invention relates to a synthetic antigen represented by the following formula (I) and enantiomers or diastereoisomers of this antigen.

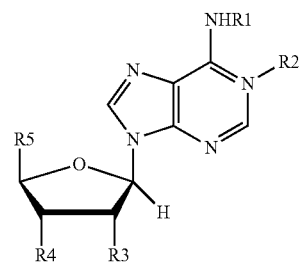

In formula (I) R1 is H or a group with formula (II)

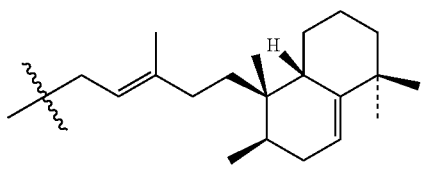

R2 is absent or a group with formula (II), provided that one of R1 and R2 is a group with formula (II).
R3 and R4 are selected independently from hydrogen, OH or an acyl group, in any combination thereof.
R5 is a linker group comprising a functional group which enables immobilization of the antigen to a solid substrate. and enantiomers or diastereoisomers of said antigen.

In a second aspect the invention relates to a solid substrate, comprising at least one type of antigen immobilized thereto, wherein said at least one type of antigen is represented by the following formula (I) or enantiomers and diastereoisomers thereof and mixtures thereof:

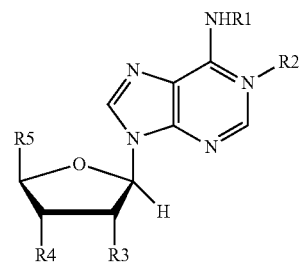

wherein in formula (I) R3 and R4 are selected independently from hydrogen, OH or an acyl group, in any combination thereof, R5 is a linker group, R1 is H or a group with formula (II)

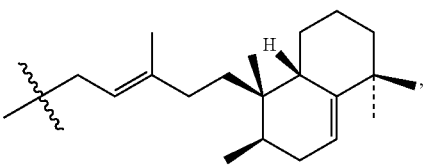

and R2 is absent or a group with formula (II), provided that one of R1 and R2 is a group with formula (II), wherein said antigen is immobilized to said solid substrate via said linker group at the R5 position.

In a third aspect the invention relates to a method for immobilizing an antigen to a solid substrate, comprising: immobilizing an antigen represented by the following formula (I) or enantiomers, diastereoisomers of the antigen, and mixtures thereof:

(I)

wherein in formula (I) R3 and R4 are selected independently from hydrogen, OH or an acyl group, in any combination thereof, and wherein R5 is a linker group, R1 is H or a group with formula (II)

(II)

and R2 is absent or a group with formula (II), provided that one of R1 and R2 is a group with formula (II), onto a solid substrate via said linker group at the R5 position.

In a fourth aspect, the invention relates to a biosensor, comprising the solid substrate according to the second aspect.

In a fifth aspect, the invention relates to a tuberculosis detection system comprising the solid substrate according to the second aspect.

In a sixth aspect, the invention relates to a method of detecting the presence of antibodies against mycobacterial material in a sample comprising the steps of:
(1) providing a sample from a human or animal;
(2) exposing at least part of the sample to synthetic antigens according the first aspect of the invention or the solid substrate of the second aspect of the invention;
(3) detecting binding of antibodies in said sample to said antigens,
wherein binding of an antibody to said antigens is indicative for the presence of mycobacterial material in a human or animal.

SHORT DESCRIPTION OF THE FIGURES

FIG. 1 shows an SPR spectrum of binding of serum antibodies to an SPR substrate to which a tuberculosinyl adenosine antigen is immobilized via a biotinylated PEG linker in accordance with the invention.

DETAILED DESCRIPTION

The synthetic antigens described herein are capable of binding to an antibody which is indicative for the presence of mycobacterial material in a human or animal. With "mycobacterial material" in this context is meant material derived from *Mycobacterium tuberculosis* which leads to generation of antibodies in a human or animal. The presence of this material indicates tuberculosis. The inventor has surprisingly found that when the above defined antigens are immobilized to a solid substrate via a linker group at the R5 position as indicated in formula (I) above, excellent antigen presentation is obtained compared to when the antigens would be immobilized, for instance, via the R3 or R4 groups. By "better presentation" it is meant that antibodies against tuberculosinyl adenosine from a sample show improved recognition of the immobilized antigens. This results in a significant improvement with regard to the sensitivity of detection of tuberculosinyl adenosine antibody markers, which on its turn results in improved detection of tuberculosis.

The tuberculosinyl adenosine derived synthetic antigen used in the present invention is represented by the following formula (I) and enantiomers or diastereoisomers thereof:

(I)

In formula (I) R1 is H or a group with formula (II)

(II)

R2 is absent or a group with formula (II), provided that one of R1 and R2 is a group with formula (II).

R3 and R4 are selected independently from hydrogen, OH or an acyl group, in any combination thereof.

R5 is a linker group. The antigen can be immobilized to a solid substrate via said linker group at R5.

In formula (I) R1 may be a group of formula (II) and R2 may be absent. In other embodiments R1 may be H and R2 may be a group of formula (II). In case R2 is a group of formula (II), the nitrogen to which it is attached carries a positive charge.

In case R3 or R4 are an acyl group it is preferred that only one of R3 and R4 is an acyl group. For instance R3 or R4 may be an amide, ester, keton or aldehyde or carboxylic acid group.

It is possible that R3 is H and R4 is OH. It is also possible that R4 is H and R3 is OH. It is also possible that both R3 and R4 are H.

It is preferred that one of R3 and R4 is OH, for instance that R4 is OH or that R3 is OH. It is preferred that R4 is OH and even more preferred that R4 and R3 are OH. Such molecules can be effectively synthesized, for instance in accordance with in accordance with the method described in Buter et al., 2016 and show good antigen presentation.

In a preferred embodiment the antigen of formula (I) is represented by a compound of formula (III) or (IV), wherein R5 is a linker group:

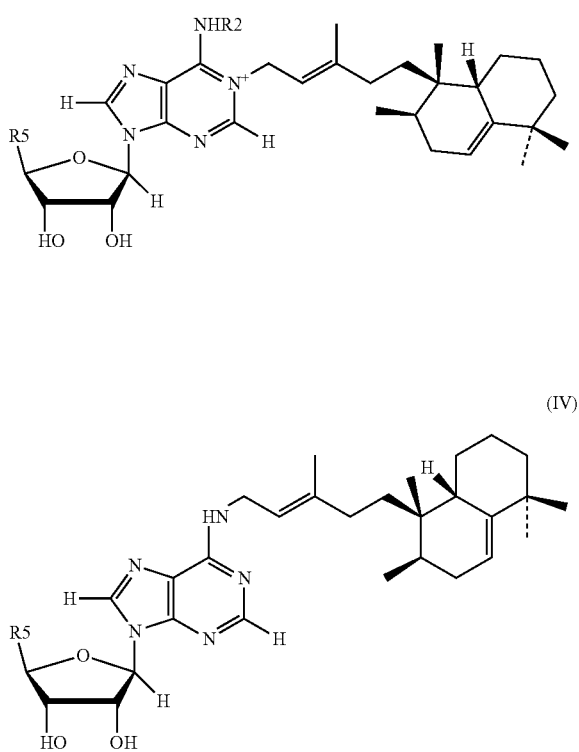

In this respect, the solid substrate according to the invention may contain any combination of antigens that are capable of binding to antibodies which are indicative for tuberculosis which fall within the definition of formula (I), for instance a combination of antigens in accordance with formula (I) comprising a compound of formula (III) and (IV). The substrate may comprise only one particular compound according to formula (I) such as only 1-tuberculosinyladenosine antigens (which are according to formula (III), only compound (IV) or any combination of these molecules. Also combinations of enantiomers or diastereoisomers are possible.

Synthetic antigens in accordance with formula (I), (III) and (IV) may for instance be synthetized in accordance with the method described in Buter et al., 2016. Linker groups may be added in accordance with available techniques in the art of organic chemistry. It is preferred in this respect that a linker-coupled adenosine moiety is prepared before the adenosine moiety is coupled to the tuberculosinyl moiety.

For purposes of detection of the presence of antibodies in a sample the antigens can be immobilized to a solid substrate which can be exposed to a sample derived from a human or animal so that binding of antibodies to the immobilized antigens can be determined, either qualitatively or quantitatively or both. It is noted that in this application the term "solid substrate" means the same as "solid surface" or "solid support".

The solid substrate may suitably be a sensing or detection surface of a surface plasmon resonance device, electrochemical impedance spectroscopy device, isothermal titration calorimetry device, bio-layer interferometry device, optical gratings device, photonic crystal device, acoustic resonant profiling device, or quartz crystal microbalance device; or a sensing or detection surface in an enzyme-linked immunosorbent assay (ELISA), a Western blotting assay, radioactive labelling assay, photospectrometric assay, immunofluorescence assay, immunoprecipitation assay, immunocytochemistry assay, immunohistochemistry assay, amperometric detection assay, voltametric detection assay, or electrochemical impedance spectroscopy assay.

In one embodiment said solid substrate is nitrocellulose.

In a further embodiment said solid substrate is an surface plasmon resonance (SPR) sensor disc.

Regarding the linker group, any linker group suitable to immobilize an antigen to a solid substrate may qualify and many linker groups suitable for immobilization of antigens are known in the art. Examples of such linkers will be discussed below.

In general, it is preferred that the linker group is somewhat hydrophilic, except when immobilization takes place by hydrophobic interactions. Hydrophilicity makes the antigens more soluble in aqueous solutions and thus easier in use. The increased hydrophilicity makes the detection surface or sensor surface to which the antigens are immobilized more hydrophilic. Because of this, interactions of antibodies in the antigen occur easier and the speed of the detection will be enhanced. Moreover, it will be easier to synthesize the antigens in case synthetic antigens are used.

In order to enable immobilization to a solid substrate, the linker preferably contains a functional group that enables immobilization to the substrate. The term "functional group" in this application is therefore to be understood as a group that enables immobilization of the antigen to a solid substrate. For this purpose said linker group may comprise a functional group selected from a thio group, an amine group, an aldehyde group, an azide group, a polyhistidine, or a biotin group.

A suitable linker for purposes of this invention is a polyethylene glycol (PEG linker) appropriately functionalized to enable immobilization. In a preferred embodiment said linker group is a PEG (polyethylene glycol) containing a functional group that enables immobilization to a solid substrate. Many suitable PEG linkers are available and many ways are suitable to couple the antigens to a solid substrate. The PEG group may for instance be functionalized with group comprises a functional group selected from a thio group, an amine group, an aldehyde group, an azide group, a polyhistidine, or a biotin group. In one embodiment the linker group may therefore be a biotinylated PEG group. In another embodiment said linker group may be a PEG group which contains an azide group, for instance as shown in formula (V) below.

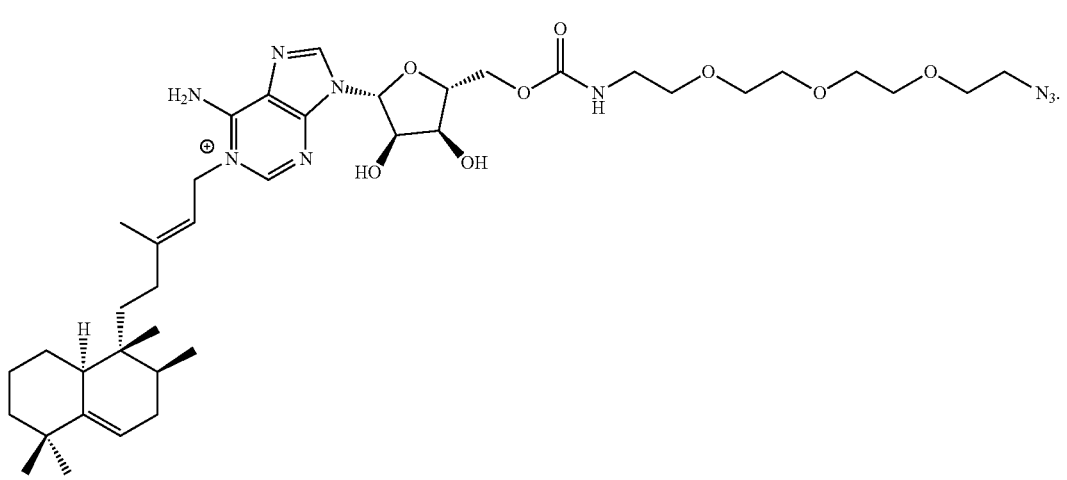

(V)

The solid substrate according to the invention may therefore be obtained by immobilizing onto said substrate at least an antigen according to formula (V). In this case immobilization takes place via azide coupling, optionally by coupling another functional group such as biotin to the linker by means of said azide. An exemplary antigen according to the invention may for instance be the antigens below according to formula (VI):

Some coupling methods require that apart from the antigen also the solid substrate to which the antigens are coupled is modified. Said substrate may be modified with a group selected from carboxymethyldextran, carboxymethylcellulose, carboxymethylpolyethyleneglycol, streptavidin derivatized carboxymethyldextran, biotin derivatized carboxymethyldextran, disulfide modified carboxymethyldextran, NTA derivatized carboxymethyldextran, polycarboxylate,

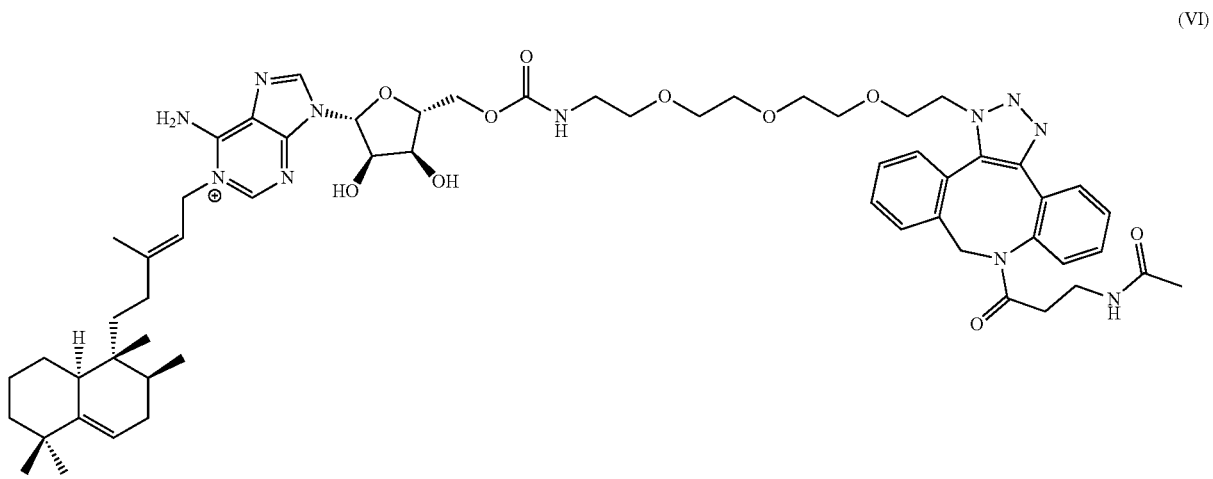

(VI)

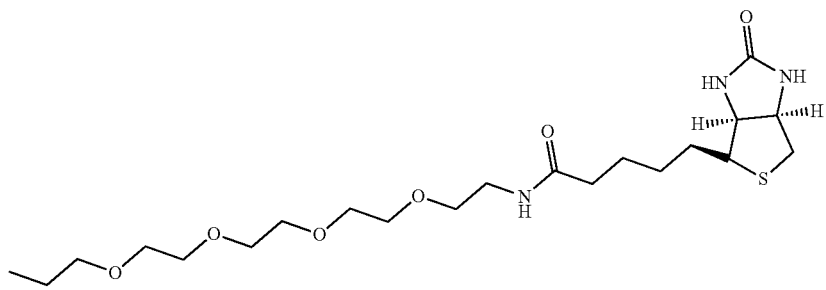

biotin derivatized polycarboxylate, hydrazide derivatized linear polycarboxylate, disulfide modified linear polycarboxylate, poly-L-lysine, hyaluronic acid, gelatin, alginate. Further examples of modified substrates include:

- NHS ester-activated support materials, wherein NHS esters are reactive groups formed by EDC activation of carboxylate molecules to react with primary amines on the antigen;
- Aldehyde-activated support materials, wherein coupling of the antigen takes place by a reaction called reductive amination;
- Azlactone-activated support materials, involving co-polymerization of acrylamide with azlactone;
- CDI-activated support materials, wherein carbonyl diimidazole (CDI) activates hydroxyls to form reactive imidazole carbamates that form carbamate linkages with primary amine-containing/modified antigens;
- Sulfhydryl-reactive support materials, wherein the thiol group can be used for direct coupling reactions;
- Maleimide-activated support materials, wherein maleimide-activated reagents form stable thioether linkages;
- Iodoacetyl-activated support materials, which react with sulfhydryl groups resulting in stable thioether linkages;
- Pyridyl disulfide support materials, wherein pyridyl disulfides react with sulfhydryl groups; and
- Hydrazide-activated support materials.

Antigens can be immobilized or "coupled" directly to solid support material by formation of covalent chemical bonds between particular functional groups on the (modified) antigen (e.g., primary amines, sulfhydryls, carboxylic acids, aldehydes) and reactive groups on the support material. It is also possible that antigens are immobilized non-covalent binding such as hydrophobic interaction or via streptavidin-biotin coupling. In case of immobilization based on hydrophobicity the linker should be equipped with a suitable hydrophobic terminus.

Various coupling methods are possible. For instance, thio coupling, amine coupling and carbonyl-reactive immobilization methods, which involve coupling through carbonyl (sugar) groups where cis-diols can be oxidized with sodium periodate to create aldehydes as sites for covalent immobilization. Also self-assembly immobilization methods are possible.

For instance, a silica based substrate may be modified with a silane derivative containing a free amine group, e.g. aminopropyltriethoxysilane or aminomethoxysilane. This free amine group reacts spontaneously with a thiol modified antigen to form a covalent bond. This does not require complicated protocols.

In case of gold solid substrates, such as SPR substrates, a thiol cysteamine monolayer may be applied to the gold substrate. The free amine of the thiol cysteamine may than be applied in a spontaneous coupling reaction with a thiol-modified antigen. This would not require complicated protocols.

If SPR sensor discs are used as solid substrate, these may be modified with a planar (2D) coating or a 3D hydrogel matrix. Planar coatings may include biotin, covalently immobilized on a saccharide monolayer, carboxymethyldextran surface; carboxymethylated dendritic polyglycerol; carboxymethylated tetraethylene glycol monolayer; carboxyl functionalized self-assembled alkyl monolayer; dextran surface; polycarboxylate surface; hydrophobic planar alkyl layer; hydrazomodified carboxyl surface; partially alkyl derivatized carboxymethyldextran surface; NTA derivatized chelating surface; hydroxyl functionalized self-assembled alkyl monolayer; Protein A/G derivatized carboxymethyldextran surface; streptavidin derivatized carboxymethyldextran surface; tetraethylene glycol monolayer; disulfide modified carboxymethyldextran surface; UV photocrosslinker derivatized carboxymethyldextran; UV photocrosslinker derivatized polycarboxylate surface. 3D hydrogel matrices may include agarose hydrogel; alginate hydrogel; biotin, immobilized in a carboxymethyldextran hydrogel; biotin, immobilized in a linear polycarboxylate hydrogel; linear polycarboxylate hydrogel; carboxymethylcellulose hydrogel; carboxymethyldextran hydrogel; carboxymethyl polyethyleneglycol; hydrazide derivatized linear polycarboxylate hydrogel; partially alkyl derivatized carboxymethyldextran hydrogel; NTA derivatized carboxymethyldextran hydrogel; NTA derivatized linear polycarboxylate hydrogel; protein A/G derivatized carboxymethyldextran hydrogel; protein A/G derivatized linear polycarboxylate hydrogel; polyethyleneglycol; Poly-L-lysine; streptavidin derivatized carboxymethyldextran hydrogel; streptavidin derivatized linear polycarboxylate hydrogel; disulfide modified carboxymethyldextran hydrogel; disulfide modified linear polycarboxylate hydrogel; UV photocrosslinker derivatized carboxymethyldextran hydrogel; UV photocrosslinker derivatized polycarboxylate hydrogel; zwitterionic polycarboxylate hydrogel; zwitterionic polycarboxylate hydrogel, positively charged, NHS preactivated; polycarboxylate hydrogel, partially sulfonated; dextran hydrogel; gelatin hydrogel; polycarboxylate hydrogel; heparin; polycarboxylate hydrogel; hyaluronic acid hydrogel.

Regarding coupling to nitrocellulose membranes, coupling may be based on various mechanisms. An unmodified antigen may be immobilized to the membrane with a hydrophobic moiety as discussed above, but other mechanisms are also possible. Such mechanisms include covalent attachment of thiolated antigen to an epoxide-functionalized nitrocellulose membrane, attachment of a biotinylated antigen through a nitrocellulose-binding streptavidin anchor protein, and fusion of an antigen to a novel nitrocellulose-binding anchor protein for direct coupling and covalent attachment through an epoxide thiol linkage using a functionalized nitrocellulose membrane immobilization.

In further embodiment immobilization takes place via avidin-biotin interaction. As avidin, for instance streptavidin or neutravidin may be coupled to the solid substrate, for instance an SPR substrate, while the linker of the tuberculosinyl antigen is functionalized with a biotin moiety to enable coupling to the avidin modified solid substrate surface. A suitable synthetic antigen for this purposes may for instance be the antigen according to formula (VI):

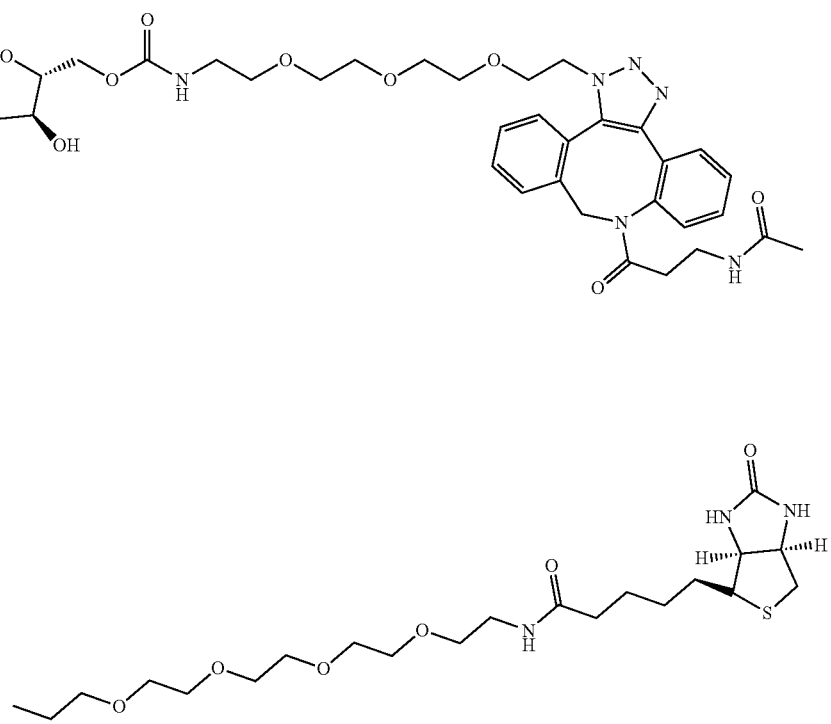

(VI)

The invention also relates to a biosensor. The immobilized antigens can be incorporated in a biosensor which can be used in the method of the invention. Such a biosensor can be any biosensor which is suitable for use in any of the abovementioned devices or assays. For instance, the biosensor may comprise a silica based substrate with immobilized antigens and a Si ring resonator. Such a biosensor can be used for ring resonance. It is also well possible that the substrates of the chambers of the biosensor are gold based. Gold based substrates are particularly useful when surface plasmon resonance or electrochemical impedance spectroscopy are used to detect binding of antibodies to the immobilized antigens. The invention also encompasses any other biosensor comprising the solid substrate of the invention.

The invention also relates to a tuberculosis detection system comprising the solid substrate according to the invention. This tuberculosis detection system may therefore comprise the biosensor according to the invention. The tuberculosis detection system is suitable to carry out a method for detection of of detecting the presence of antibodies against mycobacterial material in a sample in accordance with the invention.

This method comprises the steps of:
(1) providing a sample from a human or animal;
(2) exposing at least part of the sample to synthetic antigens in accordance with the invention;
(3) detecting binding of antibodies in said sample to said antigens,
wherein binding of an antibody to said antigens is indicative for the presence of mycobacterial material in a human or animal. In this method it is preferred that the synthetic antigens are immobilized to a solid substrate, therefore it is preferred that in step (2) said at least a part of the sample is exposed to the solid substrate according to the invention.

In one embodiment this method further comprises detecting binding of antibodies in said sample to one or more further types of immobilized antigen. Such antigens may include mycolic acid derivatives, diacyl glycolipids, mannosyl phosphoketide antigens and derivatives of these antigens in any combination, such as for instance in the combinations and variations as defined and described in earlier applications WO2017/211314 A1 and WO2017/211316 A1 of the present applicants.

In the method of the invention, one or more samples from a human or animal may be compared to a sample from a human or animal which is confirmed to be healthy and to a sample from a human or animal which is confirmed to have tuberculosis. For the sake of reliability it is highly preferred that all samples in one analysis undergo the same treatment in accordance with the steps of the method of the invention. In the method of the invention a sample from a human or animal is provided. Normally the sample is derived from a human or animal which is suspected of having active tuberculosis, for instance a human or animal that had contact with someone suffering from tuberculosis or who resides in an area or travelled to an area with high prevalence of tuberculosis.

The sample may be obtained by any regular means of obtaining blood from a subject. In order to be used in the methods of the invention samples may be used that have been collected at an earlier stage, stored until use under suitable conditions and provided at a suitable moment. Alternatively, a sample may be used in the detection method of the invention on the spot, i.e. as a point of care test.

The sample is preferably a blood derived sample. The sample may be a whole blood sample, a plasma sample or a serum sample. Blood serum is blood plasma without clotting factors and is preferred as plasma. The word plasma in this application may therefore as well refer to (blood)

serum. Serum is preferred because it contains less different materials than blood plasma, which may lead to a specific interactions or unwanted biological activity. In addition, serum may have a lower viscosity than blood plasma. Using serum therefore may circumvent the need for diluting a sample, which saves time and materials.

In case the sample is a whole blood sample, the sample is preferably pre-filtered or separated to plasma or serum. A suitable filter for such a pre-filtering step is a 0.2 micron filter.

About 55% of whole blood consists of plasma/serum. If a whole blood sample is not filtered sufficiently or if the patient's physical situation necessitates it, it may be desired to dilute the whole blood sample or plasma or serum. The words plasma or serum in this application may therefore also refer to diluted plasma or serum. A dilution of the blood or plasma may therefore be implemented in the method of the invention, such as 5 to 10×dilution, a 10 to 20×dilution, a 20 to 50×dilution, a 50 to 100×dilution, a 250 to 5000×dilution, a 750 to 1250×dilution, such as for instance a 5×, 10×, 20×, 50×, 100×, 200×, 500×, 4000×, 2000× or 1000×dilution. Depending on the viscosity of the sample, such dilution may take place before the step of separating the plasma from the blood step (filter step or separating step). Alternatively dilution may take place after the filter step.

Dilution may be performed with any suitable diluent, for example a PBS based buffer, such as a blocking buffer.

The whole blood sample or plasma or serum may be further diluted with agents that prevent blood clotting, such as EDTA, heparine or citrate.

Optionally a detergent may be added in low concentration to the blood/plasma/serum to avoid sticking of components of the test system used.

For detection at least part of the sample is exposed to a solid substrate carrying the immobilized antigen, i.e. to a detection substrate, and binding of antibodies to the antigen is detected.

Binding of the antibodies to the immobilized antigens can be detected by means of any assay that involves measurement of change of mass on the substrate, change of refractive index, change of entropy, change of enthalpy, viscosity change, temperature change, colour change etc.

Detection of binding of antibodies to the antigen on the detection substrate may take place with any suitable detection method, including simple visual detection or methods that include voltametrical, amperometrical or any electrochemical detection.

Detection of binding of antibodies to the antigen on the detection substrate may take place in real time or by means of an end-point assay.

In a real time method, because detection takes place in real time, binding of antibodies to the antigens immobilized on the detection substrates is directly detected during the binding process. For detection in principle all real-time, label free analysis techniques may be used.

Suitable real time detection assays include surface plasmon resonance or electrochemical impedance spectroscopy, isothermal titration calorimetry, bio-layer interferometry, optical gratings, photonic crystal, acoustic resonant profiling, quartz crystal microbalances.

In a real time detection method, the solid substrate carrying the antigen may be silica based, such as substrates based on silicium dioxide. In such an embodiment the antigens are preferably modified at one or both of the acyl chains with a functional group that enables immobilization. Silica based substrates are particularly useful when ring resonance technology is used to detect binding of antibodies to the immobilized antigens. Preferably, the detection is carried out using a biosensor chip using a Si-based ring resonator. This enables the method of the invention to be carried out with a very compact device.

It is also well possible that the solid substrate is gold based. Gold based substrates are particularly useful when surface plasmon resonance or electrochemical impedance spectroscopy are used to detect binding of antibodies to the immobilized antigens.

The detection of binding of antibodies and/or other material to the antigen on the detection substrate may be carried out in an automated device. Various automated devices will be known to the person skilled in the art and the skilled person will be able to select suitable software means to determine the degree or extent of binding to the detection substrate.

Detection of binding of antibodies to the antigen on the detection substrate may also take place by means of an end-point assay. The term "end-point assay" is to be understood as an assay wherein the outcome of interest is the end result after a fixed assay incubation period, in contrast to the aforementioned real-time assay. An end-point detection assay may for instance detect changes to levels of colour, fluorescence, absorbance or luminescence at the end of a test.

Suitable end-point assays include enzyme-linked immunosorbent assay (ELISA), Western blotting, radioactive labelling assay, photospectrometric assay, immunofluorescence, immunoprecipitation, immunocytochemistry, immunohistochemistry, amperometric or voltametric detection assays, or electrochemical impedance spectroscopy.

In a preferred embodiment of an end-point assay detection takes place by means of an immunogold filtration assay. In such an assay the detection substrate is a microporous membrane, preferably a nitrocellulose membrane or a PVDF membrane, to which an antigen is immobilized.

In an end-point assay interaction of antibodies with the antigens may be carried out using secondary antibodies that bind the heavy chain of the primary antibodies that bind to the immobilized antigens. Many suitable secondary antibodies are commercially available. The secondary antibody may be coupled to nanoparticles or beads, for instance gold beads, or associated with liposomes. Examples of secondary antibodies may be protein A or G, possibly conjugated with an enzyme that enables detection.

A particular suitable technique or detecting the binding of antibodies to the immobilized antigens on the detection substrate is the so-called immunogold filtration assay (IGFA), and in particular the dot immunogold filtration assay (DIGFA).

Immunogold filtration assays are methods combining ELISA and immunogold technique and are methods in which a sample to be assayed is allowed to filtrate through a microporous membrane, preferably a nitrocellulose membrane, and is captured by a capture probe coated on the membrane. A colloidal gold-labelled probe is allowed to filtrate through the microporous membrane in the same manner. By using a microporous membrane as the carrier for the capture probe and employing the capillary action and permeability of the membrane, antigens and antibodies can easily react and may conveniently be subjected to optional washing and/or blocking steps. When the colloidal gold-labelled probe binds to the capture probe the colloidal gold particles aggregate and a red dot appears which is visible with the naked eye.

In case the end-point assay of the present invention is an immunogold filtration assay, the antigen is immobilized on a microporous membrane, preferably a nitrocellulose membrane. After immobilizing the antigen onto the microporous membrane, the optionally pre-treated samples can be applied to the membrane. After addition of the sample fractions and reaction of the immobilized antigens with the antibodies contained in the samples on the membrane, colloidal gold-labelled second antibodies can be added onto the membrane to have gold particle aggregation in the antigen-antibody reaction place. In case of aggregation visible red or brown spots are formed. The intensity of the spot is proportional to the amount of reactions between antigen and antibody, i.e. to the amount of antibodies in the sample. In other words a sample from a person suffering from tuberculosis will result in a more intense spot than a sample from a person which is healthy.

Immunogold filtration assays are simple and rapid detection methods because no instruments are required except a membrane and the reagents and the results can be observed by the naked eye within a few minutes.

In an immunogold filtration assay the microporous membrane may be for example a nitrocellulose membrane, a cellulose acetate membrane or a PVDF membrane with a suitable pore diameter. Preferably, nitrocellulose is used. A suitable pore diameter is 0.2 to 5 µm.

Between the various steps of an immunogold filtration assay the membrane may be washed with a suitable buffer, for example a PBS based buffer. Such buffer may for example be a PBS/AE buffer comprising NaCl, KCl, $KH_2PO_4$, $Na_2HPO_4$ and EDTA in water at physiological pH. Such buffer may be a PBS based buffer consisting of 8.0 g NaCl, 0.2 g KCl, 0.2 g $KH_2PO_4$, and 1.05 g $Na_2HPO_4$ per liter of double distilled, deionized water containing 1 mM EDTA and 0.025% (m/v) sodium azide which is adjusted to pH 7.4.

In case DIGFA is used, the antigen may be immobilized to the microporous membrane in a dot wise manner. In a DIGFA assay the samples are also applied to the membrane in the form of dots. Also the colloidal gold-labelled second antibodies are added in the form of dots. A DIGFA assay is particularly preferred because at different spots on several membranes various antigens deriving from various mycobacterial strains may be immobilized. This way it becomes possible to provide information on which mycobacterial strain a patient is infected with. Another advantage of using DIGFA is that samples derived from different persons can be compared in one test, because DIGFA enables fast and reliable detection of antibody-antigen interaction in an unlimited amount of spots, depending on the size of the membrane.

The detection of binding of antibodies and/or other material to the immobilized antigens, for instance the red staining in case a DIGFA assay is used as a detection method, may be carried out in an automated device. Various automated devices will be known to the person skilled in the art and the skilled person will be able to select suitable software means to quantify the degree or extent of binding on the detection substrates.

The detection of binding of antibodies and/or other material to the immobilized antigen may be performed by a visual detection technique or any other suitable detection technique. In a particular preferred embodiment, detection by means of the end-point assay takes place visually, preferably with the naked eye. This has the advantage of easy detection without the need for expensive and complicated detection technology. In case DIGFA is used, binding of antibody antibodies and/or other material to the immobilized antigens may be assessed by means of the naked eye.

A visual signal, e.g. the red staining in case a DIGFA assay is applied as end-point assay, may also be detected with help of a mobile app, i.e. a computer program designed to run on mobile devices such as tablet computers or smart phones. For instance, an app can be used that is designed to compare the binding signal between different samples or sample fractions and which indicates whether the human or animal from which the sample originated has tuberculosis.

The method of the invention may comprise additional steps that are advantageous for the sensitivity of the method. For instance the method may contain further steps of exposing the sample to molecules that have affinity for molecules in the sample that lead to a binding signal which is not specific for tuberculosis in order to scavenge away these non-specific molecules.

The method may also contain further steps of dividing the sample. The high specificity of the antigens according to formulae (I), (V) and (VI) used in accordance with the invention for tuberculosis specific antibodies and the associated lower risk of false positives also make it possible to reliably diagnose whether a person has tuberculosis without the necessity to divide a sample from a human or animal into two sample fractions of which one is exposed to antigens before the two fractions are exposed to a detection substrate with antigens. Methods that involve dividing the sample into fractions are for instance described in WO 2005/116654 and WO 2013/186679. Nevertheless, the solid substrate of the invention would be suitable in such a method. In one embodiment the method of the invention therefore may be a real-time method comprising the steps of:
  i) providing a sample from a human or animal;
  ii) obtaining at least two fractions of said sample;
  iii) exposing the first of said fractions to a solid substrate carrying immobilized antigens,
  iv) exposing the second of said fractions to a solid substrate not carrying immobilized antigens;
  v) exposing the sample fraction exposed in step iii) to a solid test substrate which is a solid substrate as described above for the second aspect of the invention and exposing the sample fraction exposed in step iv) to a solid control substrate which has the same composition as the solid test substrate;
  vi) detecting binding of antibodies to the immobilized antigens of step v) in real time; and
  vii) comparing the degree or extent of binding between the test and control substrates, any observed lesser binding to the test substrate being an indicator of the presence of antibodies to the immobilized antigen in the sample that indicates tuberculosis in the human or animal from which the samples originated, wherein the antigens immobilized to the solid substrate of step iii) comprise at least one type, preferably all the types of antigens that are immobilized to the solid test and control substrates.

In a comparable embodiment, the method of the invention may be an end-point method of detecting antibodies against mycobacterial material in a sample,
  comprising the steps of:
  i) providing a sample from a human or animal;
  ii) obtaining at least two fractions of said sample;
  iii) exposing the first of said fractions to a solid substrate carrying immobilized antigens;
  iv) exposing the second of said fractions to a solid substrate not carrying immobilized antigens; or storing at least part of the second of said fractions until step v), skipping the step of exposing the second of said fractions to a solid substrate not carrying immobilized antigens;
  v) exposing at least part of the sample fraction exposed in step iii) to a solid test substrate which is a substrate which is a solid substrate as described above for the second aspect of the invention and exposing the sample fraction exposed or stored in step iv) to a solid control substrate which has the same composition as the solid test substrate;
  vi) detecting binding of antibodies to the immobilized antigen of step v) in an end-point assay; and vii) comparing the degree or extent of binding between the test and control substrates, any observed lesser binding to the test substrate being an indicator of the presence of antibodies to the immobilized antigen in the sample that indicates tuberculosis in the human or animal from which the samples originated, wherein the antigens immobilized to the solid substrate of step iii) comprise at least one type, preferably all the types of antigens that are immobilized to the solid test and control substrates.

In the context of these embodiments it should be understood that lesser can be interpreted qualitatively and quantitatively, i.e. lesser binding may be interpreted as having less binding events as well as having weaker bindings. The advantage of these two embodiments is that no sample of a healthy person is required as a reference or control sample, even if there is still background signal. Only one sample from one subject is necessary in these embodiments.

Further, the substrate to which the antibody is immobilized in step iii) of these embodiments is in general not made of the same material as the test/control substrate. The substrate in step iii) may be made of any material that is inert for non-specific binding of molecules of the sample. Such materials include polytetrafluorethylene (e.g. Teflon®), polypropylene, polyetherketone (PEEK) and polyethylene. The test and control substrates in these embodiments are sensing surfaces or substrates of a detection device or detection surfaces or substrates in a detection assay as discussed above.

EXAMPLES

The following examples are meant to illustrate the principle of the invention and should not be interpreted as limiting the scope of the claims.

Example 1

Synthesis of Tuberculosinyl Adenosine Conjugated-PEG-Azide from Tuberculosinyl

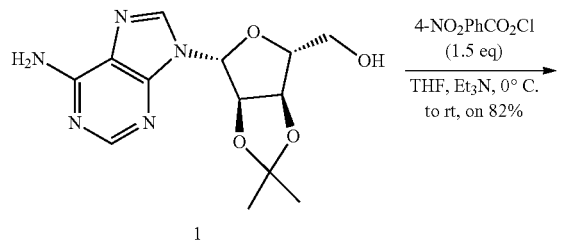

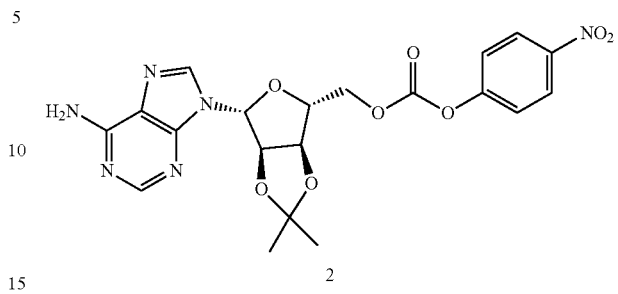

2',3'-O-Isopropylidene-5'-O-(4-nitrophenoxycarbonyl)-adenosine(2):

To a suspension of 1 (1.55 g, 5.04 mmol) in dry THF (25 mL) was added Et$_3$N (1.5 mL, 10.1 mmol, 2 eq) and 4-nitrophenyl chloroformate (1.52 g, 7.5 mmol, 1.5 eq) portion-wise at 0° C. The mixture was stirred 20 h at rt. Then, the reaction was quenched by ice and subsequently EtOAc and saturated aqueous NaHCO$_3$ (15 mL) were added. The layers were separated, and organic layer was washed with NaHCO$_3$ (15 mL) and saturated aqueous NaCl (15 mL), dried over MgSO$_4$, concentrated in vacuo. The residue was purified by column chromatography (silica gel, AcOEt/MeOH=25/1) to afford 2 (1.95 g, 82%) as a light yellow foamy solid. The NMR data matched literature.

$^1$H-NMR (400 MHz, CDCl$_3$) δ 8.33 (s, 1H), 8.22 (d, J=9.2 Hz, 2H), 7.91 (s, 1H), 7.29 (d, J=8.8 Hz, 2H), 6.15 (s, 1H), 5.98 (s, 2H), 5.52 (d, J=6.0 Hz, 1H), 5.20 (dd, J=6.0 Hz, 2.8 Hz, 1H), 4.60-4.55 (m, 2H), 4.49-4.44 (m, 1H), 1.63 (s, 3H), 1.41 (s, 3H). $^{13}$C-NMR (101 MHz, CDCl$_3$) δ 155.75, 155.34, 153.28, 152.16, 149.33, 145.55, 139.98, 125.40, 121.73, 120.40, 114.90, 91.05, 84.86, 84.36, 81.63, 68.55, 27.27, 25.49.

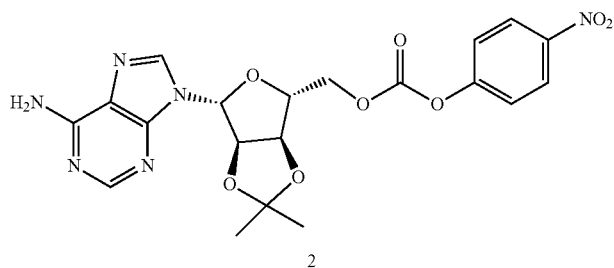

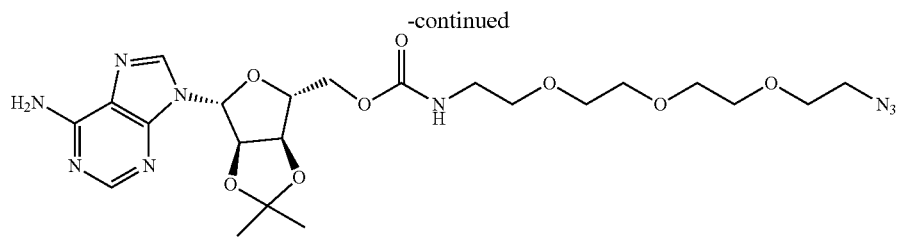

4

(((3aR,4R,6R,6aR)-6-(6-amino-9H-purin-9-yl)-2,2-dimethyltetrahydrofuro[3,4-d][1,3]dioxol-4-yl)methyl(2-(2-(2-(2-azidoethoxy)ethoxy)ethoxy)ethyl)carbamate(4):

To a solution of 2 (1.35 g, 2.85 mmol) in CHCl$_3$ (20 mL) was added Et$_3$N (0.60 mL, 4.28 mmol) and N$_3$—PEG-Azide 3 (0.6 mL, 3.02 mmol, 1.1 eq) at rt. The reaction was stirred 18 h. Thereafter, the reaction was concentrated in vacuo. The residue was purified by column chromatography (silica gel, (MeOH/CH$_2$Cl$_2$=0/100, 1/98, 3/97) to give 4 (1.2 g, 76%) as a yellow sticky oil.

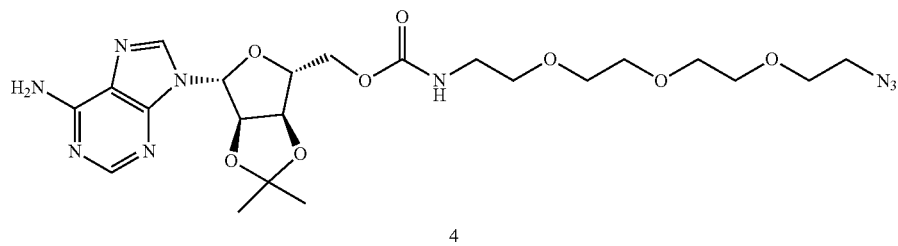

4

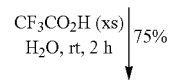

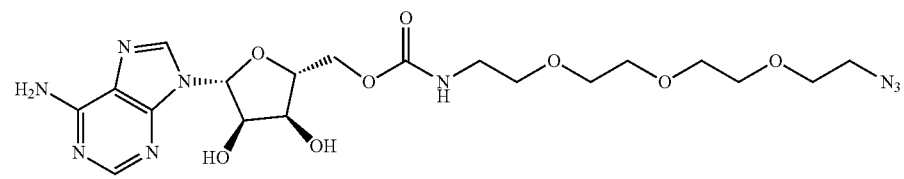

5

(((2R,3S,4R,5R)-5-(6-amino-9H-purin-9-yl)-3,4-dihydroxytetrahydrofuran-2-yl)methyl(2-(2-(2-(2-azidoethoxy)ethoxy)ethoxy)ethyl)carbamate(5):

A solution of 4 (1.01 g, 1.83 mmol) in a mixture of TFA and water (4:1, 10 mL) was stirred for 2 h. TLC indicated complete complete conversion. The reaction was concentrated under reduced pressure. The residue was co-evaporated with EtOH (3×10 mL) and CH$_2$Cl$_2$ (3×10 mL), to give a crude product as a bright yellow foam. NMR analysis of crude product indicated impurities therefore, the crude was purified by column chromatography ((MeOH/CH$_2$Cl$_2$, 0/100, 3/97, 5/95/2/8) to afford pure product (0.703 g, 75%) before starting the next step.

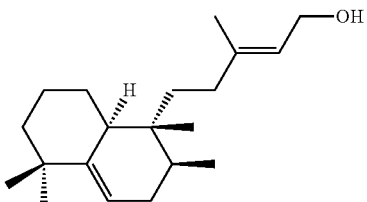

Tuberculosinol
(6)

NCS (1.3)
Me$_2$S (1.5 eq)

CH$_2$Cl$_2$, -40° C.
to rt, 2 h
97%

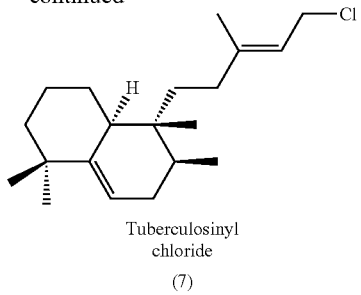

Tuberculosinyl
chloride (7)

(4aS,5R,6S)-5-((E)-5-chloro-3-methylpent-3-en-1-yl)-1,1,5,6-tetramethyl-1,2,3,4,4a,5,6,7-octahydronaphthalene(tuberculosinyl chloride):

To a suspension of N-chlorosuccinimide (0.18 g, 1.34 mmol, 1.3 eq) in dry CH$_2$Cl$_2$ (2.7 mL), cooled to −20° C., was added dropwise dimethyl sulfide (0.115 mL, 8.78 mmol, 1.5 eq) in dry CH$_2$Cl$_2$ (0.9 mL). The milky white suspension was allowed to warm to 0° C. by replacing at ice-bath for 15 min after which the reaction flask was again placed at cooling bath, which was at −40° C. Tuberculosinol (0.3 g, 1.03 mmol) in dry CH$_2$Cl$_2$ (3.5 mL) with the aid of a syringe pump over a 15 min. After addition, the cooling bath was removed and the reaction was allowed to warm-up to rt. The reaction was allowed to stir at this temperature for 2 h after which TLC indicated complete conversion of the tuberculosinol. The reaction mixture was concentrated under reduced pressure and treated with pentane upon which succinimide was oiled out. The mixture was decanted and filtered, the elute was concentrated under reduced pressure affording crude tuberculosinyl chloride (0.31 g, 97%) as a yellow oil. The crude tuberculosinyl chloride was used in the next step without purification.

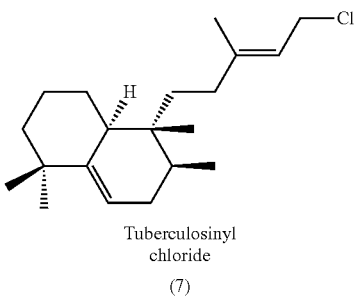

Tuberculosinyl
chloride (7)

+

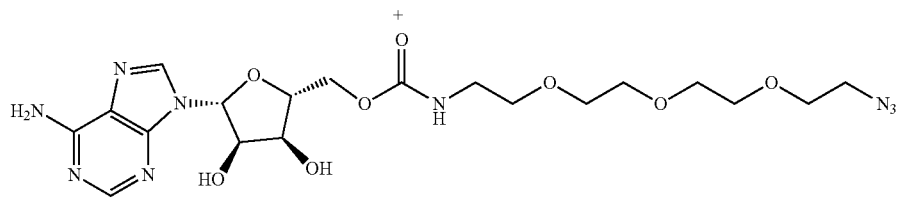

5

NaI (2 eq)
DMF, 50° C., on

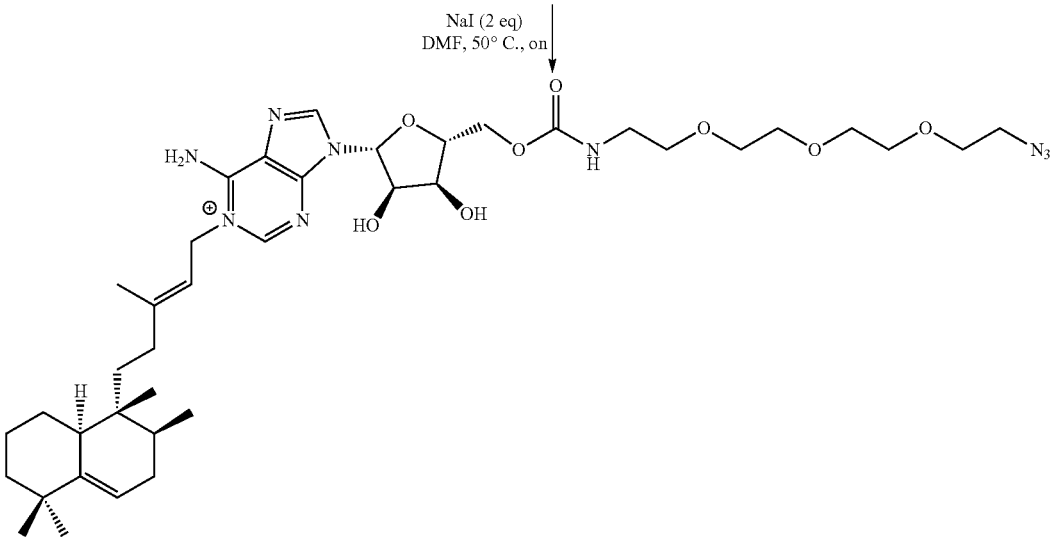

1-TbAd-PEG-N$_3$ formula (V)

6-amino-9-((2R,3R,4S,5R)-5-(15-azido-3-oxo-2,7,10,13-tetraoxa-4-azapentadecyl)-3,4-dihydroxytetrahydrofuran-2-yl)-1-((E)-3-methyl-5-((1R,2S,8aS)-1,2,5,5-tetramethyl-1,2,3,5,6,7,8,8a-octahydronaphthalen-1-yl)pent-2-en-1-yl)-9H-purin-1-ium(TbAd-PEG-N$_3$):

Crude tuberculosinyl chloride (0.2 g, 0.61 mmol) obtained in the previous step was taken in an aluminum foil rapped round bottom flask (5 mL). To the flask, DMF (1.2 mL), sodium iodide (0.11 g, 0.73 mmol, 1.2 eq) and adenosine-PEG-N$_3$ 5 (0.375 g, 0.73 mmol, 1.2 eq) were sequentially added. The resulting suspension was allowed to stir for 3 days (65 h). TLC indicated complete conversion of the starting material. The reaction mixture was concentrated under reduced pressure and subsequently purified using column chromatography (MeOH/CH$_2$Cl$_2$=1/19, 1/9 to give pure TbAd-PEG-N$_3$ as a slightly yellow foamy solid.

$^1$H NMR (400 MHz, Methanol-d$_4$) δ 8.52 (s, 1H), 8.48 (s, 1H), 6.07 (d, J=5.3 Hz, 1H), 5.51-5.43 (m, 2H), 4.93 (d, J=6.7 Hz, 2H), 4.70 (t, J=5.2 Hz, 1H), 4.33 (dddt, J=24.9, 12.9, 8.8, 3.9 Hz, 5H), 3.69-3.59 (m, 13H), 3.55 (t, J=5.4 Hz, 3H), 3.39-3.33 (m, 2H), 3.29 (d, J=5.4 Hz, 2H), 2.28-2.19 (m, 1H), 2.13-2.05 (m, 2H), 1.90 (d, J=1.3 Hz, 4H), 1.83-1.74 (m, 1H), 1.65-1.49 (m, 4H), 1.48-1.38 (m, 2H), 1.22 (td, J=12.6, 5.5 Hz, 1H), 1.10-0.99 (m, 7H), 0.92 (q, J=7.3, 6.7 Hz, 1H), 0.85 (d, J=6.7 Hz, 3H), 0.66 (s, 3H). $^{13}$C NMR (101 MHz, Methanol-d$_4$) δ 158.4, 153.9, 152.2, 148.3, 147.8, 147.6, 147.1, 144.0, 121.3, 117.4, 115.6, 90.2, 84.6, 75.6, 71.9, 71.6, 71.5, 71.5, 71.4, 71.4, 71.2, 71.2, 71.0, 70.8, 65.2, 51.7, 42.0, 41.8, 41.1, 38.1, 37.0, 35.9, 34.6, 33.9, 32.6, 30.3, 29.5, 28.6, 23.2, 17.3, 16.6, 15.6. HRMS (ESI) calcd. for C$_{39}$H$_{62}$N$_9$O$_8$$^+$ [M]$^+$ 784.472. found: 784.472.

Example 2

The TbAd-PEG-N$_3$ (corresponding to the compound according to Formula (V) as mentioned earlier in this application) and obtained as described in Example 1 was biotinylated via the azide moiety with dibenzocyclooctyne-PEG4-biotin conjugate (DBCO-4PEG-BIOTIN) in a copper free click reaction in accordance with the reaction scheme below:

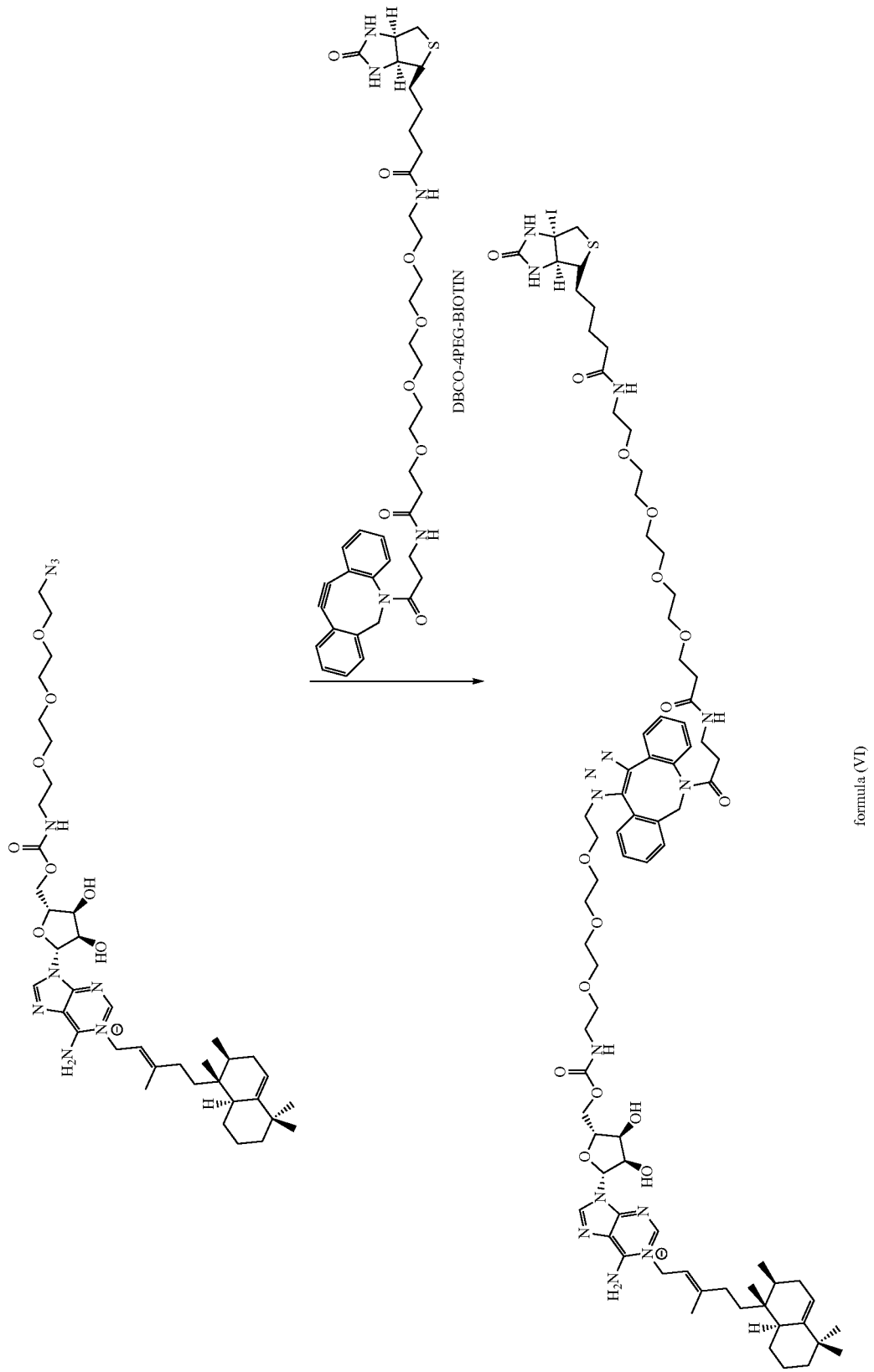

In order to carry out this reaction DBCO-4PEG-BIOTIN was dissolved in water:MeOH (50:50) for easier weighing because it is a sticky compound (5 mg in 1 mL). 0.39 mL was added to the TbAd-PEG-$N_3$ antigen and the reaction mixture was mixed and stirred at room temperature. The reaction was monitored using TLC and more DBCO-4PEG-BIOTIN was added to consume more antigen. When it was determined that the reaction of the antigen with the DBCO-4PEG-BIOTIN was complete the solvent was evaporated on rotavap and the compound was freeze dried overnight. The obtained TbAd-PEG-biotin molecule corresponds to the antigen represented by formula (VI).

Example 3

Exposure of this TbAd-PEG-biotin molecule to antibodies in serum derived from a subject that was tested positive for tuberculosis was tested by means of Surface Plasmon Resonance (SPR). For this purpose streptavidin coupled dextran modified golden SPR discs (SAHC30M, Xantec) were used in a double channel ESPRIT SPR system (Kinetic Evaluation Instruments, the Netherlands). This system has a double channel with two independent reaction areas (channels) on the same gold sensor. In a first channel Biotin-HRP was coupled via the streptavidin moiety of the sensor disc to obtain a control substrate (Biotin HRP 0.1 mg/ml). In a second channel TbAd-PEG-biotin was coupled via the streptavidin moiety of the sensor disc to obtain a test substrate 1 mg/ml TbAd-PEG-biotin in methanol/water 33%) As antigen blocking buffer PBS-gelatin was used.

In order to test whether the immobilized TbAd-PEG-biotin was able to detect TB-specific antibodies the control and test discs were exposed to a 250×diluted serum derived from a subject that was tested positive for tuberculosis in PBS gelatin.

FIG. 1 shows the results of this test. The dotted line is the base line. The serum is injected at the time point indicated with "1".

The thin dotted horizontal line at ~270 m°/26.30° C. represents a base line.

The striped line shows the spectrum of the control. Its straight line up at time point "1" indicates the refractive index change of the sample. The practically horizontal course of the HRP line immediately after time point "1" indicates that no antibody binding takes place.

The continuous line shows the spectrum of the serum interaction with the immobilized TbAd-PEG-biotin. This line represents a typical curve of specifically binding antibodies to the immobilized TbAd-PEG-biotin. The straight line up indicates the refractive index change of the sample. After this the line gradually rises, indicating binding of antibodies to the immobilized TbAd-PEG-biotin antigens on the SPR disc.

At time point "2" a washing step was started with washing buffer. As shown in the spectrum it was not possible to wash away the full signal.

FIG. 1 shows that when the antigens are immobilized to a solid substrate via a linker group at the R5 position as indicated in formula (I) above, excellent antigen presentation is obtained.

REFERENCES

WO 2005/116654

WO 2013/186679

NL 2017204 C1

WO2017/211314 A1

WO2017/211316 A1

Buter J, Heijnen D, Wan I C, Bickelhaupt F M, Young D C, Otten E, Moody D B, Minnaard A J. J Org Chem. 2016 Jul. 11.

The invention claimed is:

1. A synthetic antigen represented by the following formula (I):

(I)

wherein in formula (I):

R3 and R4 are selected independently from hydrogen, OH or an acyl group, in any combination thereof;

R5 is a linker group comprising a functional group which enables immobilization of the antigen to a solid substrate;

R1 is H or a group with formula (II)

(II)

; and

R2 is absent or a group with formula (II), provided that one of R1 and R2 is a group with formula (II);

and enantiomers or diastereoisomers of said antigen.

2. The synthetic antigen according to claim 1, wherein R4 is OH, preferably wherein R4 and R3 are OH.

3. The synthetic antigen according to claim 1, wherein said antigen is represented by a compound of formula (III) or (IV):

(III)

(IV)

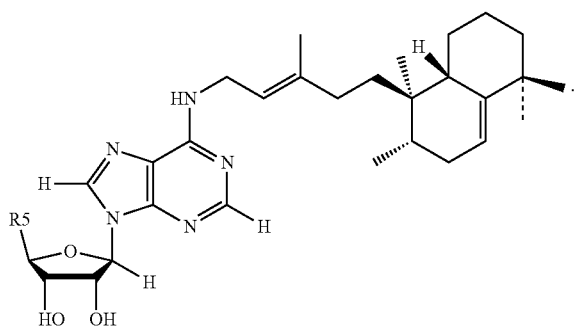

4. The synthetic antigen according to claim 1, wherein said linker group is a polyethylene glycol (PEG) group containing a functional group that enables immobilization to a solid substrate.

5. The synthetic antigen according to claim 1, wherein said linker group comprises a functional group selected from the group consisting of a thio group, an amine group, an aldehyde group, an azide group, a polyhistidine, and a biotin group.

6. The synthetic antigen according to claim 4, wherein said linker group is a biotinylated PEG group.

7. The synthetic antigen according to claim 4, wherein said linker group is a PEG group which contains an azide group.

8. A solid substrate, comprising at least one type of antigen immobilized thereto, wherein said at least one type of antigen is represented by the following formula (I) or an enantiomer or diastereoisomer thereof:

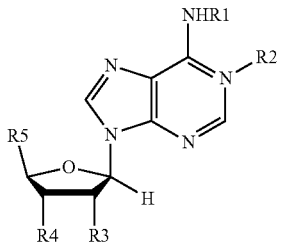

(I)

wherein in formula (I)
R3 and R4 are selected independently from hydrogen, OH or an acyl group, in any combination thereof,
R5 is a linker group;
R1 is H or a group with formula (II)

(II)

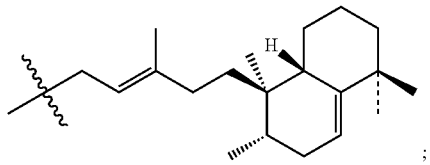

;

and
R2 is absent or a group with formula (II), provided that one of R1 and R2 is a group with formula (II);

and wherein said antigen is immobilized to said solid substrate via said linker group.

9. The solid substrate according to claim 8, obtained by immobilizing onto said substrate at least one type of antigen as defined, wherein R5 is a linker group comprising a function group which enables immobilization of the antigen to a solid substrate.

10. The solid substrate according to claim 8, wherein said substrate is a sensing or detection surface of a surface plasmon resonance device, electrochemical impedance spectroscopy device, isothermal titration calorimetry device, bio-layer interferometry device, optical gratings device, photonic crystal device, acoustic resonant profiling device, or quartz crystal microbalance device; or a sensing or detection surface in an enzyme-linked immunosorbent assay (ELISA), a Western blotting assay, radioactive labelling assay, photospectrometric assay, immunofluorescence assay, immunoprecipitation assay, immunocytochemistry assay, immunohistochemistry assay, amperometric detection assay, voltametric detection assay, or electrochemical impedance spectroscopy assay.

11. The solid substrate according to claim 8, wherein said substrate is nitrocellulose.

12. The solid substrate according to claim 8, wherein said substrate is a surface plasmon resonance (SPR) sensor disc.

13. The solid substrate according to claim 8, wherein said substrate is modified with a group selected from the group consisting of carboxymethyldextran, carboxymethylcellulose, carboxymethylpolyethyleneglycol, streptavidin derivatized carboxymethyldextran, biotin derivatized carboxymethyldextran, disulfide modified carboxymethyldextran, NTA derivatized carboxymethyldextran, polycarboxylate, biotin derivatized polycarboxylate, hydrazide derivatized linear polycarboxylate, disulfide modified linear polycarboxylate, poly-L-lysine, hyaluronic acid, gelatin, alginate and/or wherein the substrate comprises a material selected from the group consisting of a NHS ester-activated support materials, an aldehyde-activated support material, an azlactone-activated support material, CDI-activated support material, a sulfhydryl-reactive support material, a maleimide-activated support material, an iodoacetyl-activated support material, a pyridyl disulfide support material, and a hydrazide-activated support material.

14. A method for immobilizing an antigen to a solid substrate, comprising:
immobilizing at least an antigen represented by the following formula (I) or an enantiomer or diastereoisomer of said antigen:

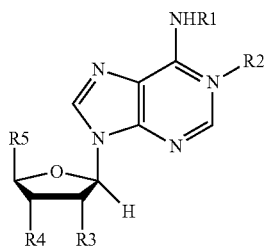

(I)

wherein in formula (I):
R3 and R4 are selected independently from hydrogen, OH or an acyl group, in any combination thereof;
R5 is a linker group;

R1 is H or a group with formula (II)

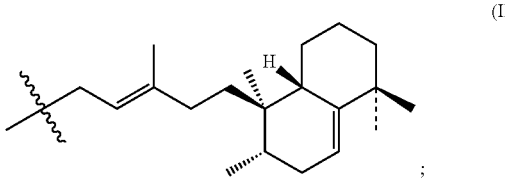

(II)

and
R2 is absent or a group with formula (II), provided that one of R1 and R2 is a group with formula (II);
onto a solid substrate via said linker group at the R5 position.

15. The method according to claim 14, wherein the antigen is as defined in formula (I).

16. The method according to the claim 14, wherein said substrate is a sensing or detection surface of a surface plasmon resonance device, electrochemical impedance spectroscopy device, isothermal titration calorimetry device, bio-layer interferometry device, optical gratings device, photonic crystal device, acoustic resonant profiling device, or quartz crystal microbalance device; or a sensing or detection surface in an enzyme-linked immunosorbent assay (ELISA), a Western blotting assay, radioactive labelling assay, photospectrometric assay, immunofluorescence assay, immunoprecipitation assay, immunocytochemistry assay, immunohistochemistry assay, amperometric detection assay, voltametric detection assay, or electrochemical impedance spectroscopy assay.

17. The method according to claim 14, wherein said substrate is selected from the group consisting of of nitrocellulose, PVDF, ELISA plate, a silicon based substrate, and an SPR sensor disc.

18. The method according to claim 14, wherein the substrate surface is modified to enable immobilization of the antigen.

19. The method according to claim 18 wherein the substrate surface is modified with a group selected from the group consisting of carboxymethyldextran, carboxymethylcellulose, carboxymethylpolyethyleneglycol, streptavidin derivatized carboxymethyldextran, biotin derivatized carboxymethyldextran, disulfide modified carboxymethyldextran, NTA derivatized carboxymethyldextran, polycarboxylate, biotin derivatized polycarboxylate, hydrazide derivatized linear polycarboxylate, disulfide modified linear polycarboxylate, poly-L-lysine, hyaluronic acid, gelatin, alginate, and/or wherein the substrate comprises a material selected from the group consisting of a NHS ester-activated support material, an aldehyde-activated support material, an azlactone-activated support material, a CDI-activated support material, a sulfhydryl-reactive support material, a maleimide-activated support material, an iodoacetyl-activated support material, a pyridyl disulfide support material, and a hydrazide-activated support material.

20. The method according to claim 14, wherein immobilization takes place via avidin-biotin interaction, such as streptavidin-biotin interaction or neutravidin-biotin interaction.

21. A biosensor, comprising the solid substrate according to claim 8.

22. A tuberculosis detection system comprising the solid substrate according to claim 8.

23. A method of detecting the presence of antibodies against mycobacterial material in a sample comprising the steps of:
(1) providing a sample from a human or animal;
(2) exposing at least part of the sample to synthetic antigens according to claim 1;
(3) detecting binding of antibodies in said sample to said antigens,
wherein binding of an antibody to said antigens is indicative for the presence of mycobacterial material in a human or animal.

24. The method according to claim 23, wherein in step (2) said at least a part of the sample is immobilized to the solid substrate via said linker group.

25. The method according to claim 23, further comprising detecting binding of antibodies in said sample to one or more further types of immobilized antigen.

26. The method according to claim 23, wherein detecting the binding of the antibodies to the immobilized antigens involves measurement of change of mass on the substrate, change of refractive index, change of entropy, change of enthalpy, viscosity change, temperature change, or colour change.

27. The method according to claim 23, wherein detection involves a technique selected from the group consisting of surface plasmon resonance, electrochemical impedance spectroscopy, isothermal titration calorimetry, bio-layer interferometry, optical gratings, photonic crystal, acoustic resonant profiling, quartz crystal microbalances, enzyme-linked immunosorbent assay (ELISA), Western blotting, radioactive labelling assay, photospectrometric assay, immunofluorescence, immunoprecipitation, immunocytochemistry, immunohistochemistry, electrochemical impedance spectroscopy, amperometric assay, voltametric assay, an immunogold filtration assay, preferably wherein the immunogold assay is a dot immunogold assay (DIGFA).

* * * * *